US012778519B2

(12) United States Patent
Lambein et al.

(10) Patent No.: US 12,778,519 B2
(45) Date of Patent: Nov. 3, 2026

(54) COMPUTER-IMPLEMENTED METHOD FOR SYNCHRONIZING A PHOTOPLETHYSMOGRAPHY (PPG) SIGNAL WITH AN ELECTROCARDIOGRAM (ECG) SIGNAL

(71) Applicant: QOMPIUM, Hasselt (BE)

(72) Inventors: Xavier Marie Christian Fernand Lambein, Rixensart (BE); Amaury Marie-Christine Christophe Vanvinckenroye, Braives (BE); Glenn De Witte, Herent (BE); Kobe Roger Marijke Leysen, Bilzen (BE); Lars Grieten, Zutendaal (BE); Jo Van Der Auwera, Meerhout (BE); Bie Josephus Constantia Van Gorp, Tielen (BE)

(73) Assignee: QOMPIUM, Hasselt (BE)

( * ) Notice: Subject to any disclaimer, the term of this patent is extended or adjusted under 35 U.S.C. 154(b) by 845 days.

(21) Appl. No.: 17/929,020

(22) PCT Filed: Nov. 19, 2020

(86) PCT No.: PCT/EP2020/082686
§ 371 (c)(1),
(2) Date: Aug. 10, 2022

(87) PCT Pub. No.: WO2021/160306
PCT Pub. Date: Aug. 19, 2021

(65) Prior Publication Data
US 2023/0157647 A1 May 25, 2023

(30) Foreign Application Priority Data
Feb. 13, 2020 (EP) .................................... 20157081

(51) Int. Cl.
*A61B 5/00* (2006.01)
*A61B 5/024* (2006.01)
(Continued)

(52) U.S. Cl.
CPC ........ *A61B 5/7285* (2013.01); *A61B 5/02416* (2013.01); *A61B 5/318* (2021.01);
(Continued)

(58) Field of Classification Search
CPC ..... A61B 5/02416; A61B 5/318; A61B 5/349; A61B 5/352; A61B 5/7221; A61B 5/7246; A61B 5/7267; A61B 5/7285
See application file for complete search history.

(56) References Cited

U.S. PATENT DOCUMENTS

| | | |
|---|---|---|
| 4,960,126 A | 10/1990 | Conlon et al. |
| 5,040,539 A | 8/1991 | Schmitt et al. |

(Continued)

FOREIGN PATENT DOCUMENTS

| | | |
|---|---|---|
| CN | 106028272 A | 10/2016 |
| WO | 2018002541 A1 | 1/2018 |

OTHER PUBLICATIONS

Pereira et al., "Photoplethysmography Based Atrial Fibrillation Detection: A Review," Jan. 10, 2020, NPJ Digital Medicine, 3, pp. 1-12. (Year: 2020).*

(Continued)

*Primary Examiner* — Sana Sahand
(74) *Attorney, Agent, or Firm* — Workman Nydegger

(57) ABSTRACT

A computer-implemented method for synchronizing a PPG signal with an ECG signal includes: recording the ECG and PPG signals semi-synchronously; cutting the PPG signal into PPG signal pieces; for a PPG signal piece: determining distances d between a vector of PPG peak times and respective vectors of ECG peak times for respective ECG signal
(Continued)

pieces obtained by applying different offsets o; determining a best matching ECG signal piece with minimal distance do; and registering start time x of the PPG signal piece, start time yo of the best matching ECG signal piece, and the minimal distance do; determining an offset and drift between the PPG signal and ECG signal as the offset and slope of a regression model modelling the relation between the start time x and start time yo, inverse weighted by the minimal distance do; applying the offset and drift to the PPG signal.

8 Claims, 5 Drawing Sheets

(51) Int. Cl.
*A61B 5/318* (2021.01)
*A61B 5/349* (2021.01)
*A61B 5/352* (2021.01)

(52) U.S. Cl.
CPC .............. *A61B 5/349* (2021.01); *A61B 5/352* (2021.01); *A61B 5/7221* (2013.01); *A61B 5/7246* (2013.01); *A61B 5/7267* (2013.01)

(56) References Cited

U.S. PATENT DOCUMENTS

| | | | | |
|---|---|---|---|---|
| 2015/0366469 | A1 | 12/2015 | Harris et al. | |
| 2018/0014752 | A1* | 1/2018 | Al-Ali | A61B 5/0816 |
| 2020/0279177 | A1* | 9/2020 | Narita | G06F 16/35 |
| 2021/0275110 | A1* | 9/2021 | Tomlinson | A61B 5/4875 |
| 2022/0183606 | A1* | 6/2022 | Wu | A61B 5/327 |

OTHER PUBLICATIONS

Lmay et al., "Wrist-Located Optical Device for Atrial Fibrillation Screening: A Clinical Study on Twenty Patients," 2016 Computing in Cardiology Conference, Sep. 11, 2016, vol. 43, pp. 681-684.

Rundo et al., "An Advanced Bio-Inspired PhotoPlethysmoGraphy (PPG) and ECG Pattern Recognition System for Medical Assessment," Sensors, vol. 18, No. 405, Jan. 30, 2018, 22 pages.

Extended European Search Report from corresponding EP Application No. 20157081.9, Sep. 8, 2020.

International Search Report from PCT Application No. PCT/EP2020/082686, Mar. 4, 2021.

* cited by examiner

COMPUTER-IMPLEMENTED METHOD FOR SYNCHRONIZING A PHOTOPLETHYSMOGRAPHY (PPG) SIGNAL WITH AN ELECTROCARDIOGRAM (ECG) SIGNAL

FIELD OF THE INVENTION

The present invention generally relates to time-synchronizing or aligning an electrocardiogram signal, abbreviated ECG signal, with a photoplethysmography signal, abbreviated PPG signal. More particularly, the invention relates to the synchronization of an ECG signal and PPG signal that are semi-simultaneously recorded, for applications wherein the ECG signal and PPG signal are the result of long recordings, typically many hours, and wherein the required synchronization accuracy is at milliseconds level.

BACKGROUND OF THE INVENTION

Photoplethysmography (PPG) is an optical technique that allows to monitor one or more physiological parameters by detecting blood-volume changes in peripheral circulation. PPG makes use of light absorption by blood to track these volumetric changes. When a light source illuminates the skin, the reflected light varies as blood flows. A light sensor then converts these variations in light reflection into a digital signal, the so-called PPG signal. PPG signals are typically recorded using a pulse oximeter or photodetector, for instance the camera integrated in an electronic device like a person's smartphone, smartwatch or other smart wearable or non-wearable device.

A distinction is made between remote PPG and contact PPG. Remote PPG is non-obtrusive for the monitored person but poses major challenges to signal detection and signal processing. As a consequence, the use of remote PPG remains limited to everyday applications like leisure or fitness as its accuracy and reliability are insufficient for medical applications. Contact PPG, wherein the measurement components are in direct contact with the skin, results in a more reliable, more accurate PPG signal that facilitates medical diagnosis.

In a medical context, contact PPG is mainly used for atrial fibrillation (AF) risk detection, the most common cardiac rhythm disorder. However, contact PPG is not yet recognized as a reliable technique to observe other cardiac rhythm disorders. Today, cardiac rhythm disorders are still typically detected via an electrocardiogram (ECG) obtained for instance by a Holter monitoring system.

Signals obtained by PPG sensors are rather sensitive to the recording conditions. Sub-optimal conditions can lead to lower or insufficient signal quality. Artefacts in PPG signals may result from motion, bad positioning of the skin with respect to the light sensor, ambient light interference, PPG waveform inversion, etc. In order to classify PPG signal portions as regular, irregular (cardiac rhythm disorder), or of insufficient quality, machine learning technology may be deployed. To become a performant classifier, the machine learning technology must be trained with training data, i.e. PPG signals that are reliably annotated.

PPG technology is not recognized as the gold standard for heart rhythm identification and as such, not a lot of annotated PPG data is available. Moreover, because of the artefacts often present in PPG data, it is a complex task to annotate PPG signals, which can result in inconsistent annotations. For instance, some people may be more confident in annotating lower quality signal data than others, leading to subjective differences in annotations.

A suggested approach to annotate PPG signals relies on semi-synchronous recording of an ECG signal and a PPG signal on a human or animal body, expert-based or algorithm-based annotating segments of the ECG signal, time-aligning or synchronizing the ECG and PPG signals, and mapping or copying the ECG segment annotations onto time-corresponding segments of the PPG signal.

The article "Wrist-Located Optical Device for Atrial Fibrillation Screening: A Clinical Study on Twenty Patients" from authors M. Lemay et al. for instance describes beat-to-beat alignment (synchronization) of an ECG signal and PPG signal, semi-synchronously collected using different devices on a single person. Once the time base of the PPG signal is transformed to match the time base of the ECG signal, expert annotations of rhythm epochs in the ECG signal are automatically projected onto the PPG signal. This leads to automated annotation of each interbeat interval in the PPG signal. In order to be able to map ECG annotations onto a PPG signal, the ECG signal and PPG signal hence must be time-synchronized. To time-synchronize the ECG signal and PPG signal, Lemay et al. apply the following steps:

- detect heartbeats in the PPG signal using systolic down-stroke detection;
- determine series of interbeat time intervals for the ECG signal and PPG signal;
- apply the dynamic time warping algorithm for beat-to-beat alignment of the two series of interbeat time intervals; and
- apply linear regression for the beat-to-beat aligned ECG signal and PPG signal to determine offset and drift between the ECG time base and PPG time base with removal of outliers via the RANSAC (random sample consensus) algorithm with residual threshold parameter set to 1 second.

The ECG-PPG time synchronization is also described in paragraph 2.3.1 of a the article "Can one detect atrial fibrillation using a wrist-type photoplethysmographic device?" from the authors S. Fallet, M. Lemay, et al., published on 15 Sep. 2018 by the International Federation for Medical and Biological Engineering 2018.

For long semi-simultaneously recorded ECG-PPG measurements, typically spanning many hours, it remains difficult to determine which ECG interval corresponds to which PPG interval because the start time of both recordings can differ substantially (offset) and in addition there might be a small difference between the documented sampling frequency and the actual sampling frequency of the recording devices (drift).

Lemay et al. doesn't describe in sufficient detail what they did. Dynamic Time warping (DTW) is a very generic method, and the difficulty to implement it is in the details. One possible way Lemay et al. did it is by applying DTW on the two sequences of RR intervals (with an RR interval being the time between two successive R waves, i.e. the waves representing early ventricular depolarisation), and then feeding each pair of matched ECG-PPG peaks into the linear regression. Tests however showed that this method does not work for day-long recordings with a lot of corruption.

To the best of the understanding, Lemay et al. have approximately 2200 beats in total and 20 patients, giving approximately 220 beats/patient. At 60 bpm (beats per minute) that means recordings span approximately 4 minutes/patient, which is extremely short compared to what is desired to produce training data for machine learning technology used in a PPG classifier. If the patients aren't moving too much, Lemay et al. have almost no motion artefacts. In those conditions, applying DTW to the whole RR sequences could work well, but for longer measurements, the technique fails.

Starting from the prior art known from Lemay et al., the technical problem faced is therefore to provide an alternative, more advanced ECG-PPG synchronisation algorithm, that performs well for long ECG-PPG measurements, typically many hours.

Various techniques for synchronizing ECG and PPG signals have already been described in patent literature, none of them being satisfactory.

According to a first type of solutions, ECG and PPG signals are recorded congruently and assumed to be synchronized, for instance because the signals are recorded by a single device using a common clock. United States Patent Application US 2015/366469 A1 for instance describes a system to continuously monitor cardiovascular health using an ECG source synchronized to a PPG source. Although the two signal sources are assumed to be synchronised, US 2015/366469 A1 remains silent on how the synchronisation is achieved and which alignment accuracy is required.

In a second type of solutions, ECG and PPG recordings are synchronized for cuffless blood pressure measurement and/or PWTT extraction. These prior art solutions refer to the importance of millisecond accuracy for the synchronisation of ECG and PPG signals. The Chinese Patent CN106028272 of Guangdong Lifesense Medical Electronic CO Ltd. for instance describes a time synchronization method for ECG and PPG signals that are used for blood pressure testing. The ECG and PPG signals are synchronized with high (millisecond) accuracy though a method relying on time differences between a master clock derived from the BLE protocol and a slave clock.

In a third type of solutions, an ECG synchronised pulse oximeter is used to record a PPG signal in synchronism with ECG recordings: U.S. Pat. Nos. 5,040,539, and 4,960,126 for instance describe such solutions. The applications wherein such ECG synchronised pulse oximeter is used are rather exotic (tooth pulp analysis, oxygen saturation measurements), as a result of which the required synchronization accuracy differs substantially from the milliseconds accuracy that is required for accurate ECG-PPG annotation mapping and generation of reliable annotated PPG training data.

Hence, it remains an object to provide an alternative, more advanced method for synchronizing an ECG signal and PPG signal, semi-synchronously recorded, that performs better in terms of accuracy for long ECG-PPG measurements, typically spanning many hours.

SUMMARY OF THE INVENTION

According to a first aspect of the invention, embodiments of the invention realize the above defined object by the computer-implemented method, for synchronizing a photoplethysmography signal, abbreviated PPG signal, with an electrocardiogram signal, abbreviated ECG signal, the method comprising:

- recording the ECG signal using an ECG monitoring system;
- recording the PPG signal, semi-synchronously with the recording of the ECG signal, using a contact PPG sensor;
- cutting the PPG signal into PPG signal pieces;
- for a PPG signal piece out of the PPG signal pieces:
  - generating a vector of PPG peak times for peaks in the PPG signal piece;
  - selecting different offsets o;
  - cutting different ECG signal pieces out of the ECG signal by applying the different offsets o in the ECG signal;
  - generating respective vectors of ECG peak times for the ECG signal pieces;
  - computing distances between the vector of PPG peak times and the respective vectors of ECG peak times;
  - determining a best matching ECG signal piece with minimal distance $d_o$ amongst the distances d; and
  - registering a start time x of the PPG signal piece in the PPG signal, a start time $y_o$ of the best matching ECG signal piece in the ECG signal, and the minimal distance $d_o$;
- determining an offset between the PPG signal and ECG signal as the offset of a regression model modelling the relation between the start time x and the start time $y_o$, inverse weighted by the minimal distance $d_o$;
- determining a drift between the PPG signal and ECG signal as the slope of the regression model; and
- applying the offset and the drift to the PPG signal to synchronize the PPG signal with the ECG signal.

Thus, the invention consists in improved ECG-PPG synchronization method allowing to time-align an ECG signal with a semi-synchronously recorded PPG signal with milliseconds accuracy, even if the ECG and PPG signals result from long recordings spanning many hours. An ECG signal and a PPG signal are recorded using different devices on a single human or animal body. The ECG signal is obtained by an ECG monitoring system, for example a Holter monitoring system. The PPG signal is obtained by a PPG sensor, for example a pulse oximeter or a smart device with camera like for instance a smartwatch, smart wristband, or smartphone. Typically, ECG signal recording starts first and PPG signal recording starts a few minutes later. Obviously, the recordings may also start in reverse order, i.e. PPG first and then ECG. The recorded PPG signal is then cut into pieces. These pieces may have a constant length in time, like for instance a predetermined amount of seconds (e.g. 15 seconds), but in alternative embodiments of the inventions, the pieces may have a variable length, like for instance a predetermined amount of cardiac beats (e.g. 20 cardiac beats).

For each PPG signal piece in a subset of PPG signal pieces, a best matching synchronization with an ECG signal piece is determined. The subset may contain all PPG signal pieces cut out of the recorded PPG signal or alternatively only part of the PPG signal pieces cut out of the recorded PPG signal, but shall always comprise a plurality of PPG signal pieces the amount of which is chosen to be relevant for regression. The best matching synchronization for a PPG signal piece is determined by testing different offsets o, cutting ECG signal pieces with start time y corresponding to the different offsets o (i.e. start time y in the ECG signal recording=start time x in the PPG signal recording+offset o), calculating distances d between the PPG signal piece and the different ECG signal pieces corresponding to the different offsets o, and selecting the optimal offset $o_o$ which gives the minimal distance $d_o$ between two vectors: a vector with ECG peak times (which varies with the tested offset o) and a vector with PPG peak times for peaks within the PPG signal piece (which is constant for the considered PPG signal piece).

For the best matching synchronization, the start time x of the PPG signal piece, the start time $y_o$ of the ECG signal piece, and the minimal distance $d_o$ are then registered. Weighted regression on the best matching tuples $(x, y_o)$ with weights $1/d_o$ allows to determine the offset between the ECG signal measurement and PPG signal measurement, and the drift between the ECG time base and PPG time base. A linear model may for instance be used to model the relation between the start time x of the PPG signal piece in the PPG signal recording vs. the start time $y_o$ of the best matching ECG signal piece in the ECG signal recording. In such case, the offset between the ECG signal and PPG signal corresponds to the horizontal axis crossing of the linear model, and the drift between the ECG signal and PPG signal corresponds to the slope of the linear model.

The method according to the invention allows performant and accurate synchronization of ECG and PPG signals, even when applied to long (many hours) simultaneously recorded ECG-PPG measurements. The method takes benefit of features (interval between peaks) that are common to both the ECG and PPG signals for determining best matches. Further, there is no need to remove outliers. An algorithm like RANSAC isn't necessary because weighted regression is done based on the minimum distance of matching vectors and the regression preferably uses the 11 norm which is more robust than the usual 12 norm. The main advantage thereof is that less parameters need to be tuned as RANSAC has two parameters that need tuning.

Embodiments of the computer-implemented method for synchronizing a PPG signal with an ECG signal according to the present invention, further comprise after cutting the PPG signal into PPG signal pieces:

performing a quality evaluation for the PPG signal pieces to retain only PPG signal pieces with a quality above a certain quality threshold.

Thus, each PPG signal piece is subject to a quality evaluation and only PPG pieces that have little corruption are retained in the subset (or as candidates for the subset) of PPG pieces for which a best matching ECG signal piece is determined. This way, insufficient quality PPG signal pieces as a result of bad quality PPG measurement, are filtered upfront and will not be considered in the regression process to determine offset and draft between PPG signal and ECG signal.

In embodiments of the computer-implemented method for synchronizing a PPG signal with an ECG signal according to the invention, computing the distances d comprises:

aligning a first peak detected in the PPG signal piece with a first peak detected in an ECG signal piece;

matching every further peak detected in the ECG signal piece with a peak detected in the PPG signal piece by selecting the closest PPG signal peak;

summing absolute time differences between pairs of matched signal peaks to obtain a distance.

Indeed, one way to determine the distance between the ECG and PPG peak sequences relies on aligning the first peak of each piece, and then matching every remaining peak of the ECG signal piece to a peak of the PPG signal piece by taking the closest in time. The total distance is the sum of the absolute time differences between all pairs of peaks for the considered signal piece. Each peak can only be matched once, and only with its direct neighbours. Lone peaks (both in the ECG signal and PPG signal) are not considered in the total distance. The time difference between the ECG peak and the matched PPG peak is then considered and this time difference is summed across all tuples of matched ECG and PPG peaks. The obtained sum represents the distance d between the PPG signal piece and the ECG signal piece obtained by applying the respective offset o in the ECG signal.

Embodiments of the computer-implemented method for synchronizing a PPG signal with an ECG signal according to the invention, further comprise:

copying annotations from the ECG signal onto the synchronized PPG signal to thereby obtain an annotated PPG signal.

In an example application, the PPG signal synchronized with a semi-synchronously recorded ECG signal through the method according to the present invention, is annotated by copying the annotations assigned to the ECG signal onto time corresponding portions of the PPG signal. The ECG signal is assumed to be annotated expert-based or algorithm-based, and copying the ECG annotations onto the synchronized PPG signal results in reliable, consistent PPG annotations.

Embodiments of the computer-implemented method for synchronizing a PPG signal with an ECG signal according to the invention, further comprise:

storing the annotated PPG signal in a database used for training in machine learning.

In an example application, the annotated PPG signal obtained through the method according to the present invention, will be stored in a database to be used later as training data for machine learning or deep learning tools as used for instance in PPG signal classifiers.

Embodiments of the computer-implemented method for synchronizing a PPG signal with an ECG signal according to the invention, further comprise:

training a neural network with said annotated PPG signal.

Thus, the annotated PPG signal obtained through the method according to the present invention and stored in a database of training data, may be used as training data for machine learning or deep learning tools as used for instance in PPG signal classifiers. A machine learning tool trained this way, shall be able to reliably detect various heart rhythms in a PPG signal (outcome=a medical diagnosis). In preferred embodiments wherein the mapping of ECG beats onto PPG beats is exploited to identify insufficient quality segments, the machine learning tool shall also be able to identify bad quality portions in a PPG signal (outcome=bad quality). The latter machine learning tools obtained through embodiments of the present invention can inform a person that another measurement is needed before a reliable medical diagnosis can be made.

In embodiments of the computer-implemented method for synchronizing a PPG signal with an ECG signal according to the invention, the annotations comprise one or more of the following:

- regular sine rhythm (SR);
- insufficient quality (IQ);
- undefined (UD);
- irregular rhythm annotations comprising:
  - atrial fibrillation (AF);
  - atrial flutter;
  - supraventricular tachycardia;
  - ventricular tachycardia;
  - sinus tachycardia;
  - bradycardia;
  - ventricular fibrillation;
  - premature atrial contraction (PAC); and
  - premature contraction (PC);

non-rhythm clinical annotations comprising:

sleep apnea.

Thus, ECG-PPG synchronization and ECG-PPG annotation mapping according to the present invention allows to detect a wider range of heart rhythm disorders whereas nowadays, PPG is typically used for AF detection only. In addition, improved ECG-PPG annotation mapping may be used to detect insufficient quality on the ECG, insufficient quality on the PPG, impossibility or insufficient quality in the mapping between ECG and PPG, as well as other non-rhythm clinical annotations, like for instance sleep apnea. The skilled person however shall appreciate that the above list of possible annotations is non-exhaustive.

According to a second aspect, the present invention relates to embodiments of a controller, the controller comprising at least one processor and at least one memory including computer program code, the at least one memory and computer program code being configured to, with the at least one processor, cause the controller to perform:

recording an electrocardiogram signal, abbreviated ECG signal;

recording a photoplethysmography signal, abbreviated PPG signal, semi-synchronously with the recording of the ECG signal;

cutting the PPG signal into PPG signal pieces;

for a PPG signal piece out of the PPG signal pieces:

generating a vector of PPG peak times for peaks in the PPG signal piece;

selecting different offsets o;

cutting different ECG signal pieces out of the ECG signal by applying the different offsets o in the ECG signal;

generating respective vectors of ECG peak times for the ECG signal pieces;

computing distances d between the vector of PPG peak times and the respective vectors of ECG peak times;

determining a best matching ECG signal piece with minimal distance $d_o$ amongst the distances d; and registering a start time x of the PPG signal piece in the PPG signal, a start time $y_o$ of the best matching ECG signal piece in the ECG signal, and the minimal distance $d_o$;

determining an offset between the PPG signal and ECG signal as the offset of a regression model modelling the relation between the start time x and the start time $y_o$, inverse weighted by the minimal distance $d_o$;

determining a drift between the PPG signal and ECG signal as the slope of the regression model; and applying the offset and the drift to the PPG signal to synchronize the PPG signal with the ECG signal.

According to a third aspect, the invention relates to embodiments of a computer program product, the computer program product comprising computer-executable instructions for causing a controller to perform at least the following:

recording an electrocardiogram signal, abbreviated ECG signal;

recording a photoplethysmography signal, abbreviated PPG signal, semi-synchronously with the recording of said ECG signal;

cutting the PPG signal into PPG signal pieces;

for a PPG signal piece out of the PPG signal pieces:

generating a vector of PPG peak times for peaks in the PPG signal piece;

selecting different offsets o;

cutting different ECG signal pieces out of the ECG signal by applying the different offsets o in the ECG signal;

generating respective vectors of ECG peak times for the ECG signal pieces;

computing distances d between the vector of PPG peak times and the respective vectors of ECG peak times;

determining a best matching ECG signal piece with minimal distance $d_o$ amongst the distances d; and registering a start time x of said PPG signal piece in said PPG signal, a start time $y_o$ of the best matching ECG signal piece in the ECG signal, and the minimal distance $d_o$;

determining an offset between the PPG signal and ECG signal as the offset of a regression model modelling the relation between the start time x and the start time $y_o$, inverse weighted by the minimal distance $d_o$;

determining a drift between the PPG signal and ECG signal as the slope of the regression model; and applying the offset and the drift to the PPG signal to synchronize the PPG signal with the ECG signal.

According to a fourth aspect, the present invention also relates to a computer readable storage medium, the computer readable storage medium comprising computer-executable instructions of a program for performing the following steps when the program is run on a computer:

recording an electrocardiogram signal, abbreviated ECG signal;

recording a photoplethysmography signal, abbreviated PPG signal, semi-synchronously with the recording of said ECG signal;

cutting the PPG signal into PPG signal pieces;

for a PPG signal piece out of the PPG signal pieces:

generating a vector of PPG peak times for peaks in the PPG signal piece;

selecting different offsets o;

cutting different ECG signal pieces out of the ECG signal by applying the different offsets o in the ECG signal;

generating respective vectors of ECG peak times for the ECG signal pieces;

computing distances d between the vector of PPG peak times and the respective vectors of ECG peak times;

determining a best matching ECG signal piece with minimal distance $d_o$ amongst the distances d; and registering a start time x of the PPG signal piece in the PPG signal, a start time $y_o$ of the best matching ECG signal piece in the ECG signal, and the minimal distance $d_o$;

determining an offset between the PPG signal and ECG signal as the offset of a regression model modelling the relation between the start time x and the start time $y_o$, inverse weighted by the minimal distance $d_o$;

determining a drift between the PPG signal and ECG signal as the slope of the regression model; and applying the offset and the drift to the PPG signal to synchronize the PPG signal with an ECG signal.

DETAILED DESCRIPTION OF EMBODIMENT(S)

Figure 1:
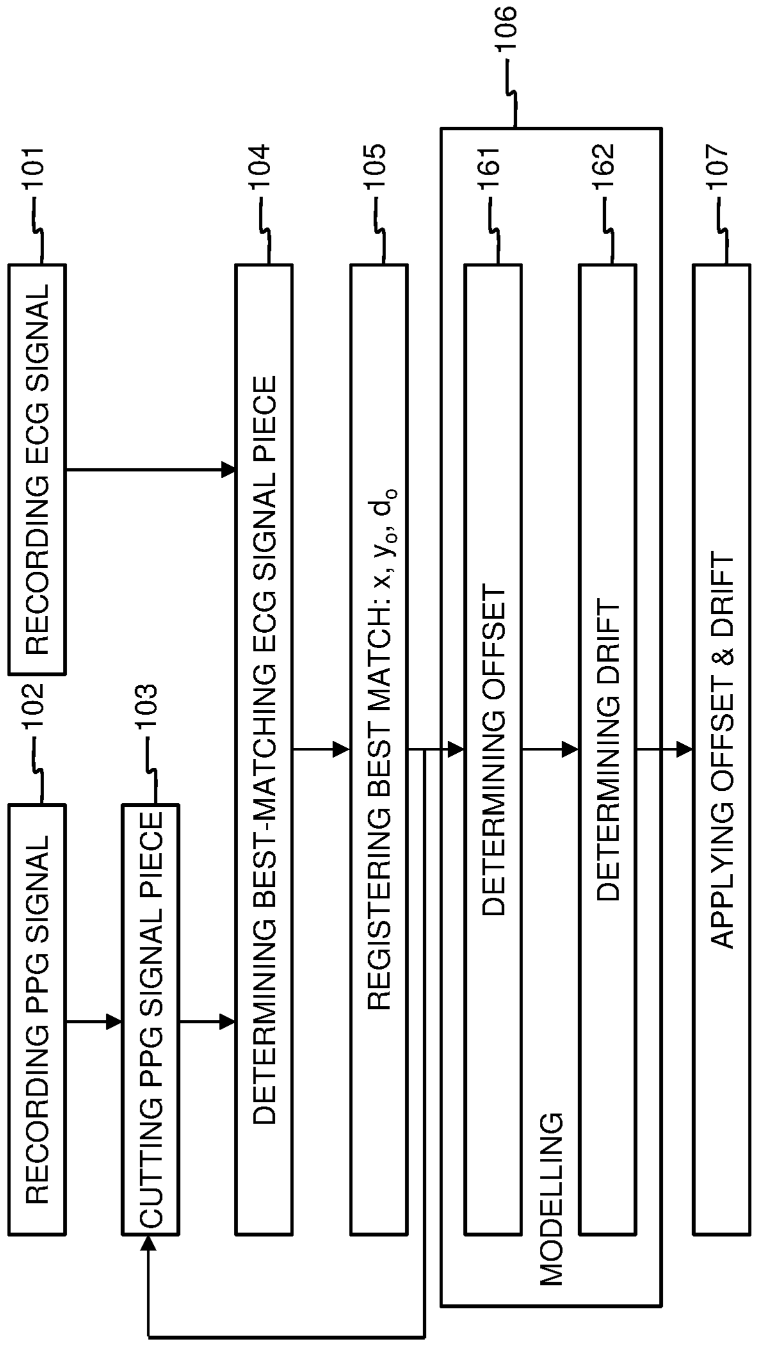
FIG. 1 is a flow scheme illustrating an embodiment of the method for synchronizing an ECG signal and PPG signal according to the present invention.

FIG. 1 shows the steps 101-107 executed in an embodiment of the method for synchronizing an ECG signal and PPG signal according to the present invention.

In steps 101 and 102, an ECG signal and a PPG signal are recorded semi-synchronously using different devices on a single person or animal. In step 101, the ECG signal is obtained by an ECG monitoring system, for example a Holter monitoring system. In step 102, the PPG signal is obtained by a PPG sensor, for example a pulse oximeter or smart device with camera, like for instance a smart wristband or smartwatch. Typically, the ECG signal recording in step 101 starts first and the PPG signal recording in step 102 starts a few minutes later. Obviously, the recordings may start in reverse order, i.e. PPG first and then ECG.

In step 103, the recorded PPG signal is cut into pieces. The pieces have a predetermined length. The predetermined length may be a fixed length in time, for example PPG signal pieces of 15 seconds each. Alternatively, the PPG signal pieces may have a predetermined length expressed as an amount of cardiac beats, for example 20 beats. In the latter example, different PPG signal pieces will have a varying duration in time. The PPG signal pieces cut out of the recorded PPG signal may be consecutive signal pieces, i.e. the next PPG signal piece starts where the previous PPG signal piece stops. Alternatively, the PPG signal pieces may be overlapping signal pieces, or they may be separated in time with start times selected randomly, pseudo-randomly, or algorithm-based. The amount of PPG signal pieces cut out of the recorded PPG signal must be high enough to enable regression modelling. This means that at least 10, but preferably a few tens or even a few hundreds of PPG signal pieces must be cut out of the recorded PPG signal.

Optionally, not shown in FIG. 1, for each PPG signal piece cut out of the recorded PPG signal a quality evaluation is performed. The quality evaluation allows to remove PPG signal pieces that are corrupted or of insufficient quality, for instance as a result of motion, bad positioning of the skin with respect to the light sensor, ambient light interference, PPG waveform inversion, etc. A possible technique to evaluate the quality of PPG signal pieces relies on Wavelet transformation and a neural network analysis. The wavelet transformed PPG signal piece is then fed into a neural network that has been trained with sets of training data to distinguish for instance good quality PPG signals, bad quality PPG signals, and inverted PPG signals. The skilled person however shall appreciate that the method according to the present invention is not limited to a particular technique for quality assessment of PPG signal pieces. The method according to the invention could even be executed without quality assessment of the PPG signal pieces. Quality assessment however brings the advantage that only PPG pieces with little or no corruption are retained for the further steps in synchronizing the PPG signal with the ECG signal, thus resulting in a more accurate synchronization.

Figure 2:
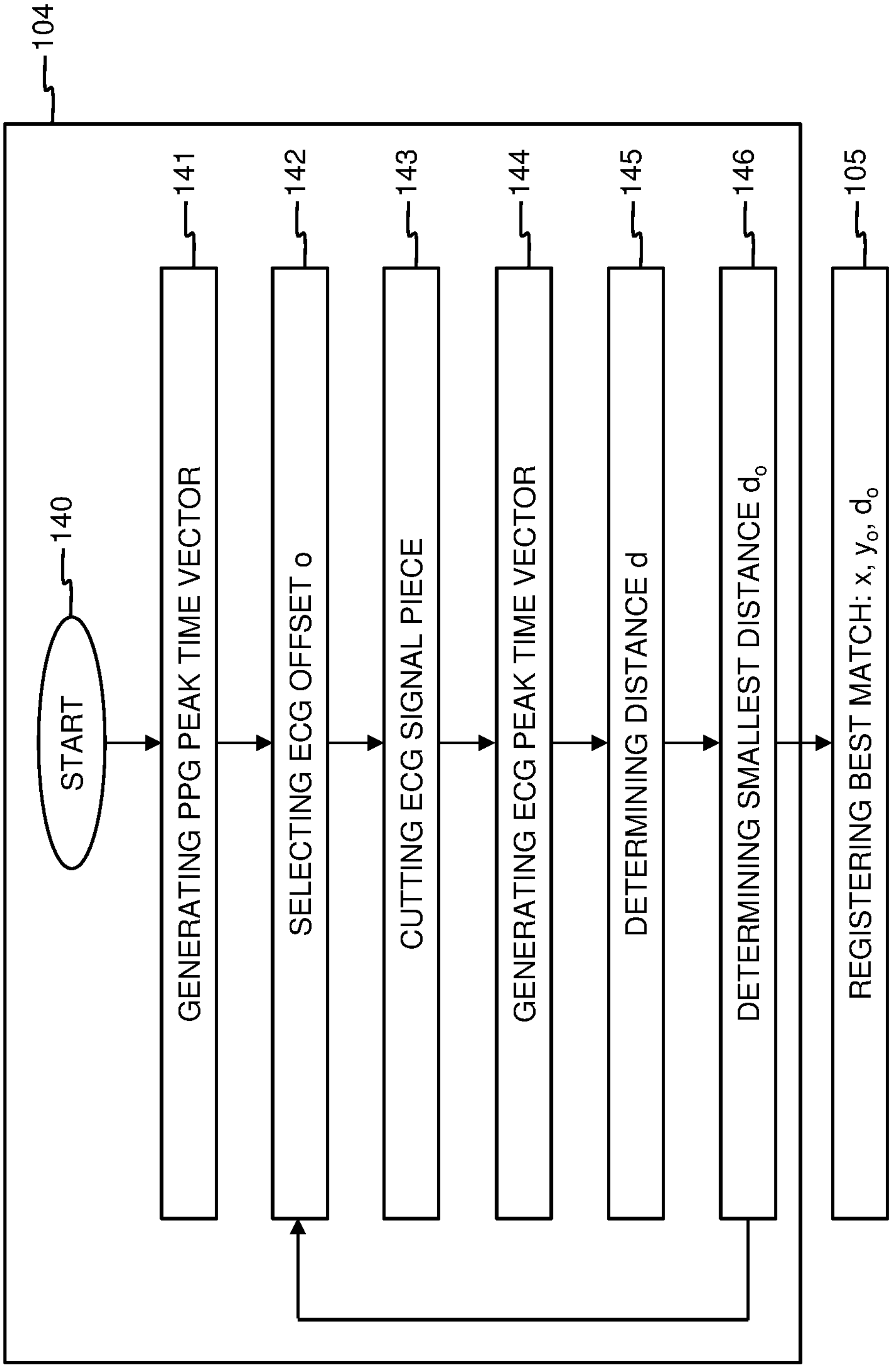
FIG. 2 is a flow scheme illustrating in more detail the step 104 of determining a best-matching ECG signal piece for a PPG signal piece in an embodiment of the method for synchronizing an ECG signal and PPG signal according to the present invention.
Figure 3:
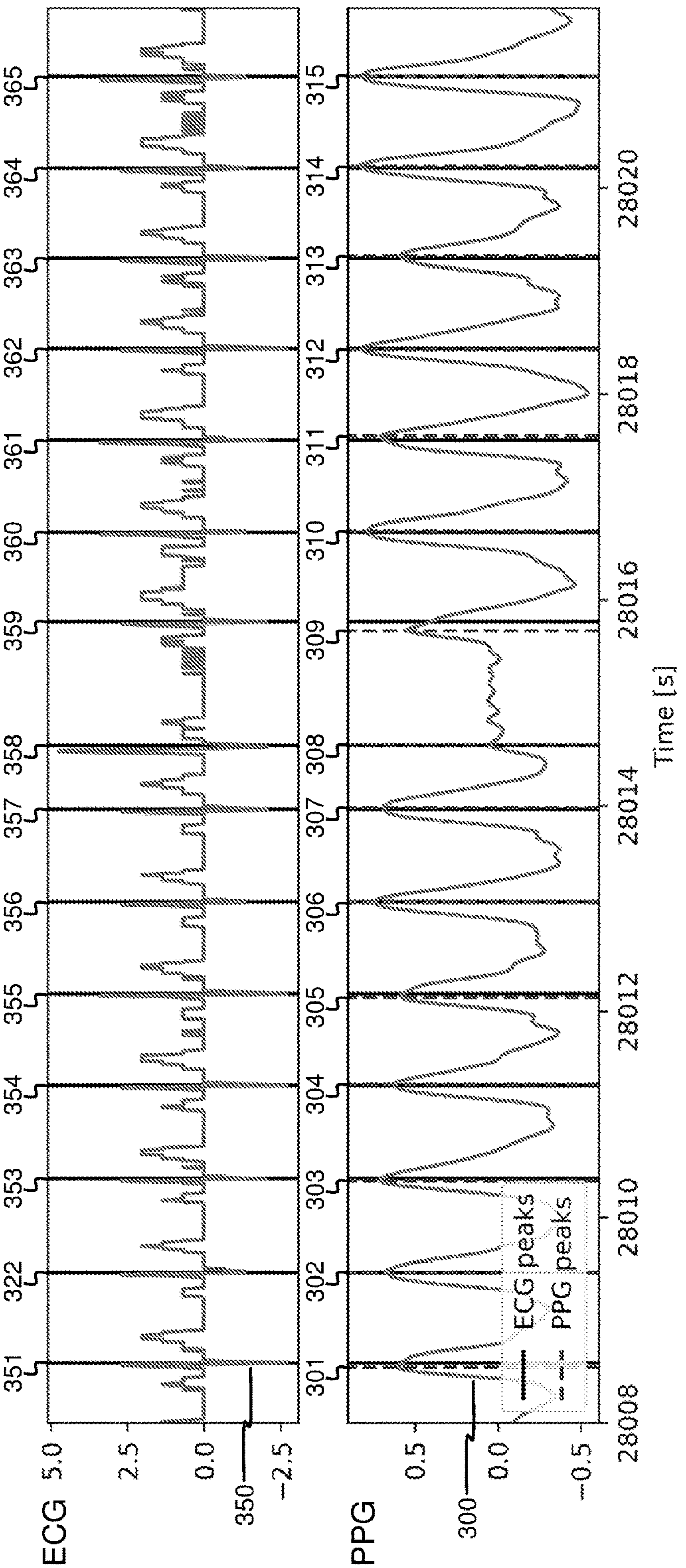
FIG. 3 shows a PPG signal piece and the best matching ECG signal piece determined by minimizing the distance between peak time vectors in step 104 of an embodiment of the method for synchronizing an ECG signal and PPG signal according to the present invention.

In step 104, for each PPG signal piece (or for each retained PPG signal piece in case an upfront quality assessment has been executed), a best matching synchronization with an ECG signal piece is determined. One possible way to determine the best matching ECG signal piece, i.e. one possible implementation of step 104, is illustrated by FIG. 2. When starting this possible implementation as is indicated by 140 in FIG. 2, a peak time vector is generated is generated for the PPG signal piece in step 141. If it is assumed for instance that signal piece 300 drawn in FIG. 3 is cut out of a recorded PPG signal, an algorithm that detects peaks or local maxima in the PPG signal piece 300 shall detect 25 PPG beats and output [301, 302, 303, 304, 305, 306, 307, 308, 309, 310, 311, 312, 313, 314, 315] as PPG peak time vector. Herein, each of the values 301-315 corresponds to the time value of a detected local maximum in the PPG time base, i.e. the time base used by the PPG sensor that records the PPG signal in step 102. The best matching ECG signal piece is then determined by iteratively testing in steps 142-146 different offsets o and selecting the optimal offset $o_o$ which has the minimal distance between two vectors: a vector with ECG peak times (which evidently varies with the tested offset o) and the PPG peak time vector [301, . . . , 315] which is constant for the considered PPG signal piece 300. In step 142, an offset value o is selected. In step 143, an ECG signal piece is cut out of the ECG signal recorded in step 101. The ECG signal piece has a start time in the recorded ECG signal that corresponds to the selected offset o, and it has a length corresponding to the predetermined length of the PPG signal piece under consideration, for instance expressed as a length in time or as an amount of beats. In step 144, an ECG peak time vector is generated for the ECG signal piece cut out of the recorded ECG signal using offset o. If for instance offset o results in ECG signal piece 350 drawn in FIG. 3 being cut out of the ECG signal, then a peak detection algorithm that detects local maxima in the ECG signal piece 350 shall output [351, 352, 353, 354, 355, 356, 357, 358, 359, 360, 361, 362, 363, 364, 365] as peak time vector for the ECG signal piece 350. Herein, the values 351-365 represent time values of local maxima in the ECG time base, i.e. the time base used by the ECG monitoring system. In step 145, the distance d is determined between the PPG peak time vector [301, . . . , 315] and the ECG peak time vector [351, . . . , 365]. This distance d between the ECG and PPG peak sequences is for example computed by aligning the first peak of the PPG signal piece 300 with the first peak of the ECG signal piece 350, and then matching every remaining peak of the ECG signal to a peak of the PPG signal piece by taking the closest PPG peak in time. Thus, tuples of peak times are generated each consisting of the peak time of an ECG peak and the closest peak time of a PPG peak. Each peak can only be matched once, and only with its direct neighbours. Lone peaks (both in ECG signal and PPG signal), like for instance the PPG peaks at times 304, 308, 312 and 315 are not considered in the total distance. The total distance d between the PPG peak time vector [301, . . . , 315] and the ECG peak time vector [351, . . . , 365] is determined as the sum of the absolute time differences between all pairs of matching ECG-PPG peaks. In step 146, the calculated distance d for offset o is compared with the smallest distance $d_o$ calculated so far for the considered PPG signal piece. If the calculated distance d is smaller than $d_o$, the value of $d_o$ will be replaced with the value of d, and the corresponding start time $y_o$ of the ECG signal piece that represents the best match with the considered PPG signal piece so far (the start time $y_o$ corresponding to the selected offset o) shall be recorded. The steps 142-146 shall be repeated thereafter for a newly selected offset value o. The steps 142-146 can be repeated until the smallest distance $d_o$ is below a predetermined threshold, or it these steps can be repeated a predetermined amount of times for a predetermined amount of offset values o ranging from $-o_m$ to $o_m$ ($o_m$ being the absolute value of a maximal allowed offset).

Summarizing, the measured PPG signal is cut into pieces of for instance 15 seconds. For each PPG signal piece located at x seconds in the PPG signal measurement, the best synchronization with an ECG signal piece located at $y_o=x+o_o$ is searched for, with $o_o$ being the optimal offset and for example $-o_m<=o_o<=o_m$ ($o_m$ being the absolute value of a maximal allowed offset). The best synchronization is determined by testing different offsets o and selecting the offset $o_o$ which has the minimal distance between two vectors, one vector with ECG peaks (which varies with the offset o and thus with the location y) and one vector with PPG peaks (which remains constant at location x). The minimal distance obtained this way is named $d_o$ and the corresponding start time of the best matching ECG signal piece is named $y_o$.

For the best matching ECG signal piece, the start time x of the PPG signal piece, the start time $y_o$ of the ECG signal piece, and the minimal distance $d_o$ are registered in step 105, as shown both in FIG. 1 and FIG. 2.

Figure 4:
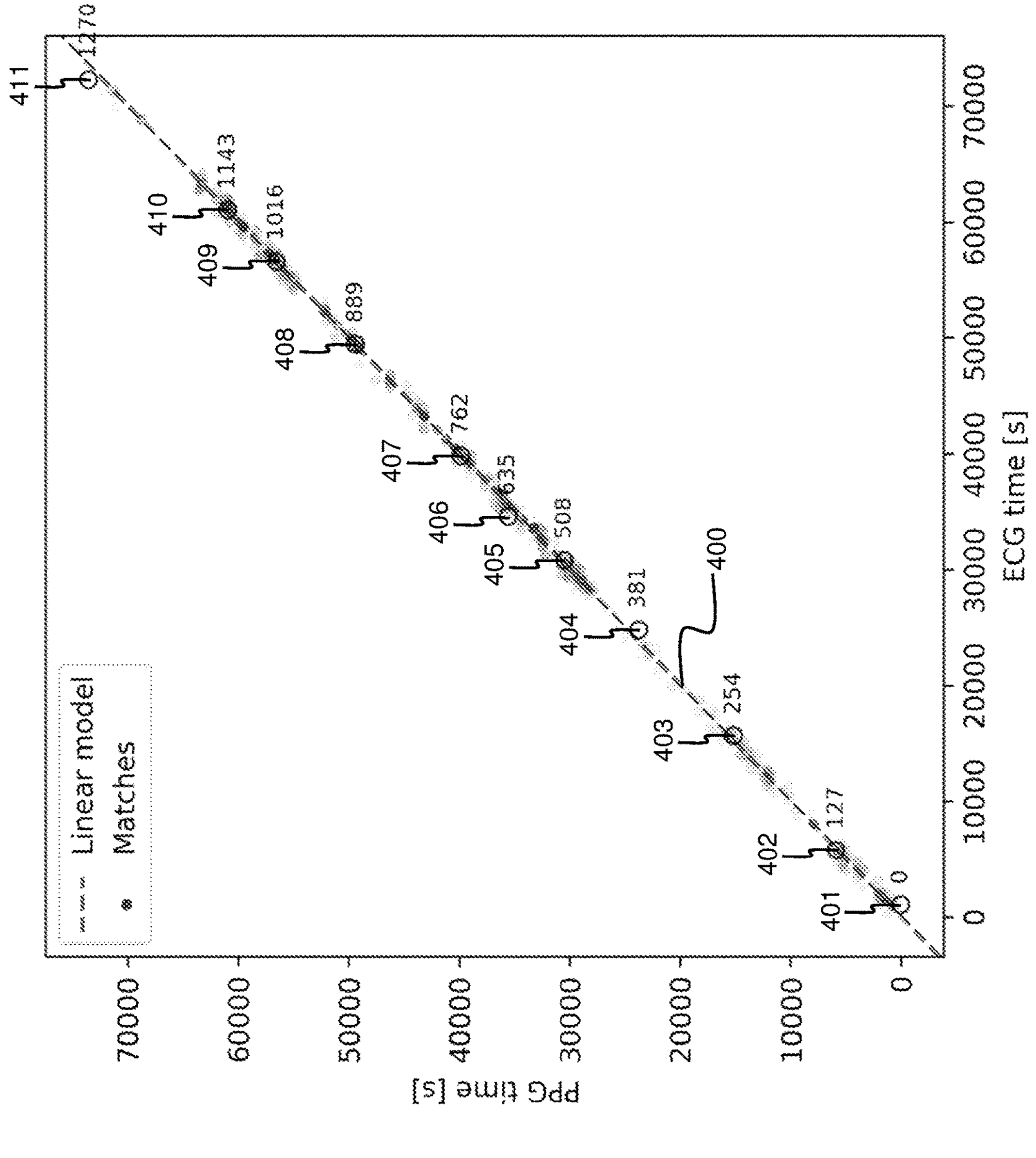
FIG. 4 is a graph showing the result of steps 105-106 of registering best matches between ECG signal pieces and PPG signal pieces, and modelling the relation between ECG time and PPG time to determine offset and drift in an embodiment of the method for synchronizing an ECG signal and PPG signal according to the present invention.

In step 106, regression modelling is applied on the best matching tuples (x, $y_o$) with x representing the start time of PPG signal pieces and $y_o$ representing the start time of the best matching ECG signal pieces. FIG. 4 for instance illustrates the result of a linear model obtained through linear regression on 11 best matching tuples represented by 401, 402, 403, 404, 405, 406, 407, 408, 409, 410 and 411. The linear regression is applied with weights $1/d_o$ such that best matching tuples with higher minimal distance do between PPG and ECG peak time vectors get a lower weight in the linear model 400. The so obtained linear model 400 allows to determine in step 161 the offset between the ECG signal and PPG signal, and in step 162 the drift between the ECG time base and PPG time base. The offset is determined as the coordinate value on the ECG time axes of the point of the linear model 400 whose PPG time=0. The drift is determined as the slope of the linear model 400. When applying the so obtained offset and drift to the ECG signal in step 107, the ECG signal and PPG signal are aligned with high accuracy and will remain synchronized over time, even if the ECG and PPG recordings last for hours.

Summarizing, weighted linear regression on the best matching tuples (x, $y_o$) with weights $d_o$ results in a linear model $y=m \cdot x+b$, with x being the PPG time (in seconds) as determined by the PPG measurement device and y being the ECG time (in seconds) as determined by the ECG monitoring system. Herein, m determines the optimal drift between ECG and PPG time, and b determines the optimal offset between ECG and PPG signal recordings for the whole measurement.

Using the offset and drift obtained through embodiments of the method according to the invention results in performant synchronization when applied to long (many hours) simultaneously recorded ECG-PPG measurements. The method takes benefit of features (the interval between peaks) that are common to both the ECG and PPG signals for determining best matches. There is no need to remove outliers. An algorithm like RANSAC isn't necessary because weighted regression is done based on the minimum distance of matching vectors and the regression may use the 11 norm which is more robust than the usual 12 norm. The main advantage thereof is that less parameters need to be tuned (RANSAC has two parameters that need tuning).

Figure 5:
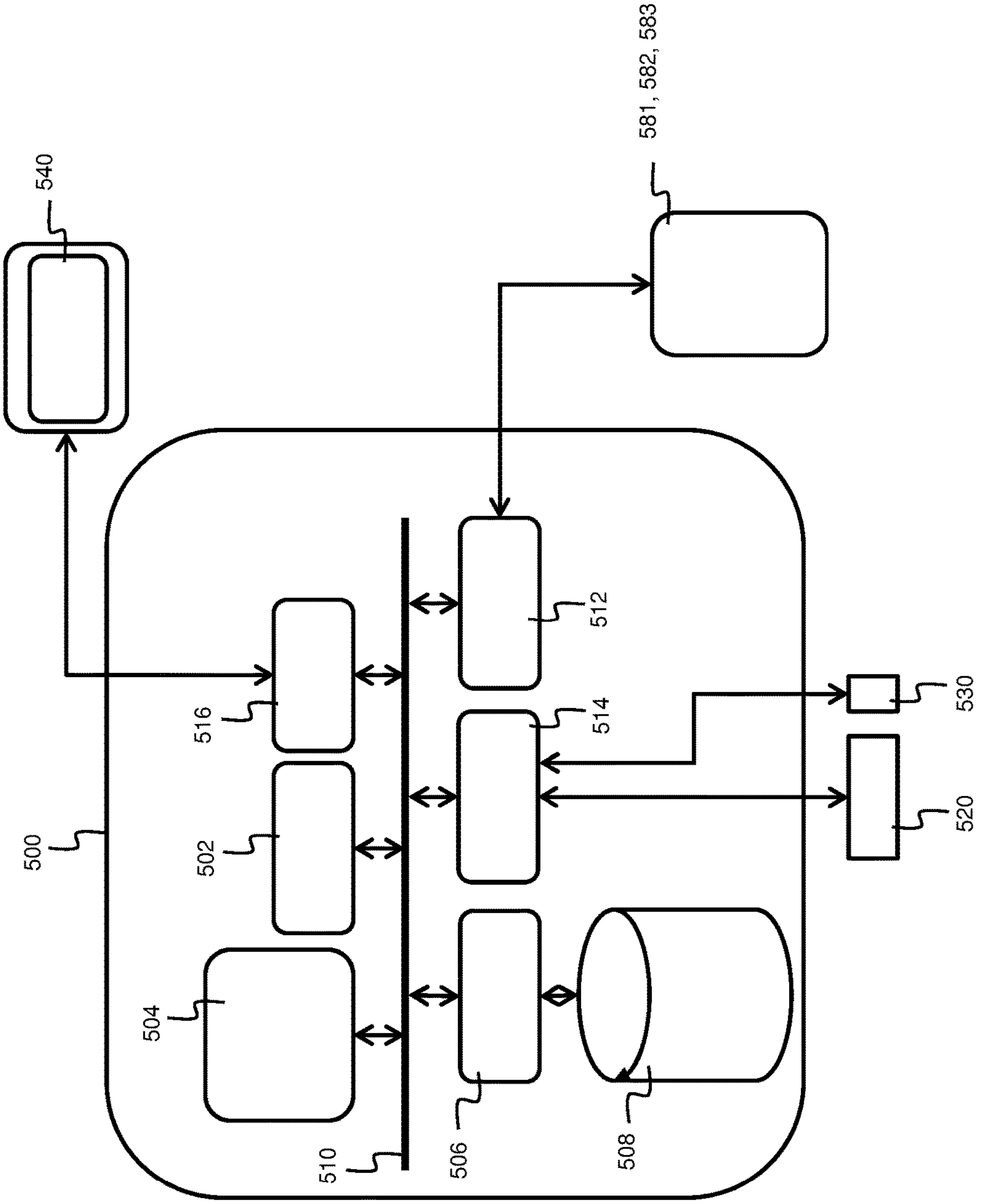
FIG. 5 illustrates a suitable computing system 500 for realizing embodiments of the method for synchronizing an ECG signal and PPG signal according to the present invention.

FIG. 5 shows a suitable computing system 500 according to an embodiment of the invention. Computing system 500 is suitable for implementing embodiments of the method for synchronizing a PPG signal with an ECG signal in line with the present invention. Computing system 500 may in general be formed as a suitable general-purpose computer and comprise a bus 510, a processor 502, a local memory 504, one or more optional input interfaces 514, one or more optional output interfaces 516, a communication interface 512, a storage element interface 506 and one or more storage element 508. Bus 510 may comprise one or more conductors that permit communication among the components of the computing system 500. Processor 502 may include any type of conventional processor or microprocessor that interprets and executes programming instructions. Local memory 504 may include a random access memory (RAM) or another type of dynamic storage device that stores information and instructions for execution by processor 502 and/or a read only memory (ROM) or another type of static storage device that stores static information and instructions for use by processor 502. Input interface 514 may comprise one or more conventional mechanism that permit an operator or user to input information to the computing device 500, such as a keyboard 520, a mouse 530, a pen, voice recognition and/or biometric mechanisms, a camera, etc. Output interface 516 may comprise one or more conventional mechanisms that output information to the operator or user, such as a display 540, etc. Communication interface 512 may comprise any transceiver-like mechanism such as for example one or more Ethernet interfaces that enables computing system 500 to communicate with other devices and/or systems, for example with other computing devices 581, 582, 583. The communication interface 512 of computing system 500 may be connected to such another computing system by means of a local area network (LAN) or a wide area network (WAN) such as for example the internet. Storage element interface 506 may comprise a storage interface such as for example a Serial Advanced Technology Attachment (SATA) interface or a Small Computer System Interface (SCSI) for connecting bus 510 to one or more storage elements 508, such as one or more local disks, for example SATA disk drives, and control the reading and writing of data to and/or from these storage elements 508. Although the storage elements 508 above is described as a local disk, in general any other suitable computer-readable media such as a removable magnetic disk, optical storage media such as a CD or DVD, -ROM disk, solid state drives, flash memory cards, . . . could be used. It is noticed that the entire method according to the present invention can be executed centralized, e.g. on a server in a management centre or in a cloud system, or it can be partially executed on a remote electronic device, e.g. worn by the user, and partially on a central server. Computing system 500 could thus correspond to the processing system available centrally or the processing system available in the electronic device.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A computer-implemented method for synchronizing a photoplethysmography signal, abbreviated PPG signal, with an electrocardiogram signal, abbreviated ECG signal, said method comprising:

recording said ECG signal using an ECG monitoring system;

recording said PPG signal, semi-synchronously with said recording of said ECG signal, using a contact PPG sensor;

cutting said PPG signal into PPG signal pieces;

for a PPG signal piece out of said PPG signal pieces:

generating a vector of PPG peak times for peaks in said PPG signal piece;

selecting different offsets o;

cutting different ECG signal pieces out of said ECG signal by applying said different offsets o in said ECG signal;

generating respective vectors of ECG peak times for said ECG signal pieces;

computing distances d between said vector of PPG peak times and said respective vectors of ECG peak times;

determining a best matching ECG signal piece with minimal distance $d_0$ amongst said distances d; and registering a start time x of said PPG signal piece in said PPG signal, a start time $y_0$ of said best matching ECG signal piece in said ECG signal, and said minimal distance $d_0$;

determining an offset between said PPG signal and ECG signal as the offset of a regression model modelling the relation between said start time x and said start time $y_0$, inverse weighted by said minimal distance $d_0$;

determining a drift between said PPG signal and ECG signal as the slope of said regression model; and applying said offset and said drift to said PPG signal to synchronize said PPG signal with said ECG signal;

wherein synchronizing said PPG signal with said ECG signal includes copying annotations from said ECG signal onto said synchronized PPG signal to thereby obtain an annotated PPG signal.

2. The computer-implemented method for synchronizing a PPG signal with an ECG signal according to claim 1, further comprising after cutting said PPG signal into PPG signal pieces:

performing a quality evaluation for said PPG signal pieces to retain only PPG signal pieces with a quality above a certain quality threshold.

3. The computer-implemented method for synchronizing a PPG signal with an ECG signal according to claim 1, wherein computing said distances d comprises:

aligning a first peak detected in said PPG signal piece with a first peak detected in an ECG signal piece;

matching every further peak detected in said ECG signal piece with a peak detected in said PPG signal piece by selecting the closest PPG signal peak;

summing absolute time differences between pairs of matched signal peaks to obtain a distance.

4. The computer-implemented method for synchronizing a PPG signal with an ECG signal according to claim 1, further comprising:

storing said annotated PPG signal in a database used for training in machine learning.

5. The computer-implemented method for synchronizing a PPG signal with an ECG signal according to claim 4, further comprising:

training a neural network with said annotated PPG signal.

6. The computer-implemented method for synchronizing a PPG signal with an ECG signal according to claim 1, wherein said annotations comprise one or more of the following:

regular sine rhythm;

insufficient quality;

undefined;

irregular rhythm annotations comprising:

atrial fibrillation;

atrial flutter;

supraventricular tachycardia;

ventricular tachycardia;

sinus tachycardia;

bradycardia;

ventricular fibrillation;

premature atrial contraction; and premature contraction;

non-rhythm clinical annotations comprising:

sleep apnea.

7. A controller comprising at least one processor and at least one memory including computer program code, the at least one memory and computer program code being configured to, with the at least one processor, cause the controller to perform:

recording said ECG signal using an ECG monitoring system;

recording said PPG signal, semi-synchronously with said recording of said ECG signal, using a contact PPG sensor;

cutting said PPG signal into PPG signal pieces;

for a PPG signal piece out of said PPG signal pieces:

generating a vector of PPG peak times for peaks in said PPG signal piece;

selecting different offsets o;
cutting different ECG signal pieces out of said ECG signal by applying said different offsets o in said ECG signal;
generating respective vectors of ECG peak times for said ECG signal pieces;
computing distances d between said vector of PPG peak times and said respective vectors of ECG peak times;
determining a best matching ECG signal piece with minimal distance $d_0$ amongst said distances d; and
registering a start time x of said PPG signal piece in said PPG signal, a start time $y_0$ of said best matching ECG signal piece in said ECG signal, and said minimal distance $d_0$;
determining an offset between said PPG signal and ECG signal as the offset of a regression model modelling the relation between said start time x and said start time $y_0$, inverse weighted by said minimal distance $d_0$;
determining a drift between said PPG signal and ECG signal as the slope of said regression model; and
applying said offset and said drift to said PPG signal to synchronize said PPG signal with said ECG signal;
wherein synchronizing said PPG signal with said ECG signal includes copying annotations from said ECG signal onto said synchronized PPG signal to thereby obtain an annotated PPG signal.

8. A computer readable storage medium comprising computer-executable instructions of a program for performing the following steps when the program is run on a computer:
recording said ECG signal using an ECG monitoring system;
recording said PPG signal, semi-synchronously with said recording of said ECG signal, using a contact PPG sensor;
cutting said PPG signal into PPG signal pieces;
for a PPG signal piece out of said PPG signal pieces:
generating a vector of PPG peak times for peaks in said PPG signal piece;
selecting different offsets o;
cutting different ECG signal pieces out of said ECG signal by applying said different offsets o in said ECG signal;
generating respective vectors of ECG peak times for said ECG signal pieces;
computing distances d between said vector of PPG peak times and said respective vectors of ECG peak times;
determining a best matching ECG signal piece with minimal distance $d_0$ amongst said distances d; and
registering a start time x of said PPG signal piece in said PPG signal, a start time $y_0$ of said best matching ECG signal piece in said ECG signal, and said minimal distance $d_0$;
determining an offset between said PPG signal and ECG signal as the offset of a regression model modelling the relation between said start time x and said start time $y_0$, inverse weighted by said minimal distance $d_0$;
determining a drift between said PPG signal and ECG signal as the slope of said regression model; and
applying said offset and said drift to said PPG signal to synchronize said PPG signal with said ECG signal;
wherein synchronizing said PPG signal with said ECG signal includes copying annotations from said ECG signal onto said synchronized PPG signal to thereby obtain an annotated PPG signal.

* * * * *